US012778706B2

(12) United States Patent
Clevett

(10) Patent No.: US 12,778,706 B2
(45) Date of Patent: Nov. 3, 2026

(54) MODULAR CONNECTION MECHANISM FOR PIN-GUIDED INSTRUMENTS

(71) Applicant: Arthrex, Inc., Naples, FL (US)

(72) Inventor: James Tyler Clevett, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 219 days.

(21) Appl. No.: 18/762,748

(22) Filed: Jul. 3, 2024

(65) Prior Publication Data

US 2025/0017681 A1 Jan. 16, 2025

Related U.S. Application Data

(60) Provisional application No. 63/526,311, filed on Jul. 12, 2023.

(51) Int. Cl.
*A61B 90/00* (2016.01)
*A61B 17/16* (2006.01)
*A61B 17/00* (2006.01)

(52) U.S. Cl.
CPC .... *A61B 90/08* (2016.02); *A61B 2017/00486* (2013.01)

(58) Field of Classification Search
CPC .......... A61B 90/08; A61B 2017/00486; A61B 2017/00477; A61B 17/162; B23B 51/12; B23B 31/11; B23B 31/1115; B23B 31/1122; B23B 31/113; B23B 31/117; A61M 25/09
USPC ...................................................... 606/79–85
See application file for complete search history.

(56) References Cited

U.S. PATENT DOCUMENTS 4,641,551 A 2/1987 Pascaloff
4,854,788 A * 8/1989 Okinaga ................ B28D 1/041 408/57
4,943,182 A 7/1990 Hoblingre
5,013,194 A * 5/1991 Wienhold ........... B23B 31/1071 279/22
5,417,527 A * 5/1995 Wienhold ............. B25B 21/007 408/239 R
5,499,984 A 3/1996 Steiner et al.
5,676,678 A 10/1997 Schad
5,720,749 A 2/1998 Rupp
5,888,200 A * 3/1999 Walen ....................... B25F 3/00 606/167
6,162,226 A * 12/2000 DeCarlo, Jr. ........ A61B 17/164 408/202
6,209,886 B1 4/2001 Estes et al.
(Continued)

FOREIGN PATENT DOCUMENTS

CN 115484876 A 12/2022
WO WO-8204209 A1 * 12/1982 ......... B23B 31/1075

*Primary Examiner* — Jessica Weiss
(74) *Attorney, Agent, or Firm* — Price Heneveld LLP

(57) ABSTRACT

A surgical accessory includes a shaft extending along a longitudinal axis from a distal head to a proximal engagement surface. At least one rib or land protrudes from the shaft along an intermediate portion between the distal head and the proximal engagement portion. The rib or land may form at least one flute at a helix angle along the intermediate portion. A detent is connected along the proximal engagement surface and engages a complimentary retention feature of a receiving socket in a coupled arrangement forming a coupling interface.

20 Claims, 12 Drawing Sheets

(56) References Cited

U.S. PATENT DOCUMENTS

| | | | | |
|---|---|---|---|---|
| 6,347,914 | B1 * | 2/2002 | Boyle | B23B 31/1072 408/226 |
| 6,689,138 | B2 * | 2/2004 | Lechot | B23B 31/117 606/80 |
| 7,060,071 | B2 * | 6/2006 | Steiger | A61B 17/1617 606/80 |
| 7,066,940 | B2 | 6/2006 | Riedel et al. | |
| 7,658,740 | B2 * | 2/2010 | Shores | A61C 1/10 606/86 R |
| 9,447,803 | B1 * | 9/2016 | Fu | A61B 17/8875 |
| 9,763,680 | B2 | 9/2017 | Fritzinger et al. | |
| 9,814,469 | B2 * | 11/2017 | Dannoritzer | B23B 31/107 |
| 9,827,001 | B2 | 11/2017 | Casey et al. | |
| 9,873,155 | B1 * | 1/2018 | Wienhold | B23B 31/22 |
| 9,949,755 | B2 * | 4/2018 | Hanson | A61B 17/3476 |
| 10,157,495 | B2 | 12/2018 | Lambert | |
| 11,331,106 | B2 * | 5/2022 | Fenn | A61B 17/162 |
| 2004/0220554 | A1 * | 11/2004 | Lechot | A61B 17/1666 606/1 |
| 2006/0259055 | A1 * | 11/2006 | Thorne | A61B 17/162 606/180 |
| 2014/0056658 | A1 * | 2/2014 | Maeda | B23C 5/109 407/40 |
| 2015/0016906 | A1 * | 1/2015 | York | B27G 15/00 408/1 BD |
| 2021/0071479 | A1 * | 3/2021 | Deen | E21B 10/43 |
| 2021/0290253 | A1 * | 9/2021 | Sweitzer | A61B 17/162 |
| 2022/0211391 | A1 | 7/2022 | Carusillo et al. | |
| 2022/0281014 | A1 * | 9/2022 | Davis | B23B 31/11 |

* cited by examiner

MODULAR CONNECTION MECHANISM FOR PIN-GUIDED INSTRUMENTS

CROSS-REFERENCE TO RELATED APPLICATIONS

This application claims priority under 35 U.S.C. § 119 (e) and the benefit of U.S. Provisional Application No. 63/526,311 entitled MODULAR CONNECTION MECHANISM FOR PIN-GUIDED INSTRUMENTS, filed on Jul. 12, 2023, by James Tyler Clevett, the entire disclosure of which is incorporated herein by reference.

BACKGROUND

The present disclosure generally relates to an apparatus for the interchangeable attachment of accessories for surgical instruments. More particularly, the disclosure relates to a connection interface or mechanism and corresponding surgical tools configured for rapid exchange and installation.

SUMMARY

Surgical accessories may necessarily be changed or swapped to successfully follow sequential steps required for various procedures. While such steps may be integral to procedures, the time associated with the removal and assembly of surgical equipment may result in delays that are not attributable to the anatomical or procedural steps required to ensure patient outcomes. In other words, though updating and reconfiguring surgical equipment and tools may be necessary, any unnecessary time or delays attributed to surgical equipment extends procedure time without providing a benefit to the outcome of the patient. Accordingly, the disclosure provides surgical accessories that may improve and simplify the associated operation to avoid procedural delays.

In some implementations, the disclosure may provide for a coupling interface configured for use in coordination with procedures that utilize guide pins or guide wires to orient surgical tools and/or cutting accessories for improved consistency and accuracy. As provided, a pin or wire-guided instrument may be cannulated and include an interior passage or cannula extending along a longitudinal axis extending from a distal or acting end through a coupling interface. In this configuration, the cannula formed through the distal or acting end of a surgical accessory may receive the guide pin or wire, such that the longitudinal axis of the surgical tool is aligned with a guide axis of the pin or wire. In various operations, surgical procedures may require that cannulated surgical accessories (e.g., drills, reamers, boring bars, etc.) may be sequentially exchanged to effectuate a desired modification to one or more anatomical structures (e.g., bones, joints, etc.) of a patient. The disclosure provides for the implementation of various surgical accessories compatible with pin or wire guided procedures while ensuring that attached surgical accessories are easily exchanged without limiting the efficacy of the corresponding surgical tools.

In various implementations, the disclosure may provide for a surgical accessory comprising a shaft extending along a longitudinal axis from a distal head to a proximal engagement surface. At least one rib or land may protrude from the shaft along an intermediate portion between the distal head and the proximal engagement portion. The rib or land may form at least one flute at a helix angle along the intermediate portion. A detent may be connected along the proximal engagement surface and engage a complimentary retention feature of a receiving socket in a coupled arrangement forming a coupling interface.

In some implementations, the disclosure may provide for a coupling interface for a surgical tool that includes a socket adapter and a surgical accessory. The socket adapter may include an adapter body having a receiving opening formed by an interior wall. At least one engaging protrusion may extend into the receiving opening from the interior wall. The surgical accessory may include a shaft extending along a longitudinal axis from the distal head to a proximal engagement surface. At least one rib or land may protrude from the shaft and spiral along an intermediate portion of the shaft between the distal head and the proximal engagement portion. The at least one rib may form at least one flute at a helix angle along the intermediate portion. In a connected configuration between the surgical accessory and the socket adapter, the shaft is received within the receiving opening and the engaging protrusion rotationally engages the at least one flute along the helix angle, thereby engaging the surgical tool to the socket adapter.

In yet another implementation, the disclosure provides for a socket adapter for a surgical accessory. The socket adapter may include an adapter body extending from a proximal end portion to a distal end portion. The distal end portion may comprise a receiving opening formed by an interior wall. A cannula may extend through the body from the proximal end portion to the distal end portion. At least one engaging protrusion may extend into the receiving opening from the interior wall at the distal end portion. Further, a retaining aperture may be formed by the interior wall and the intermediate portion between the proximal end portion and the distal end portion. The retaining aperture may be configured to receive a detent of an engagement portion of the surgical accessory.

These and other features, objects and advantages of the present disclosure will become apparent upon reading the following description thereof together with reference to the accompanying drawings.

DETAILED DESCRIPTION

Figure 1B:
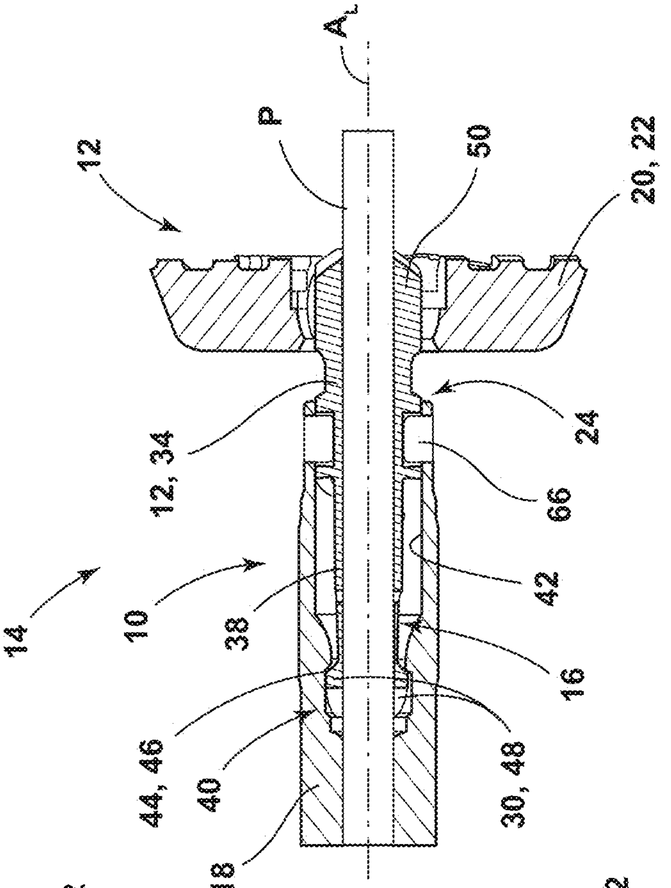
FIG. 1B is a partially hidden, side assembly view of a coupling interface and surgical accessory engaging a guide pin or wire.

In the following description, reference is made to the accompanying drawings, which show specific implementations that may be practiced. Wherever possible, the same reference numbers will be used throughout the drawings to refer to the same or like parts. It is to be understood that other implementations may be utilized, and structural and functional changes may be made without departing from the scope of this disclosure.

Referring to FIGS. 1-5, exemplary coupling interfaces 10 and corresponding surgical accessories 12 are shown demonstrating various features of a modular connection assembly 14 for pin-guided or wire-guided surgical procedures. As best demonstrated in FIGS. 1B and 2, a guide pin P or guide wire is shown engaged within a cannula 16 extending through the surgical accessory 12 and a socket adapter 18 that are mechanically engaged to form the coupling interface 10. In this configuration, a manual or powered drive assembly may engage the socket adapter 18 to securely drive a surgical tool 20 along a longitudinal axis $A_L$ aligned with the guide pin P extending through the cannula 16. As shown, the surgical tool 20 corresponds to a large surface area reamer 22. However, in various implementations, the surgical tool 20 may correspond to various cutting tools including, but not limited to, drills, mills or end mills, boring tools, threading tools, etc.).

Figure 2:
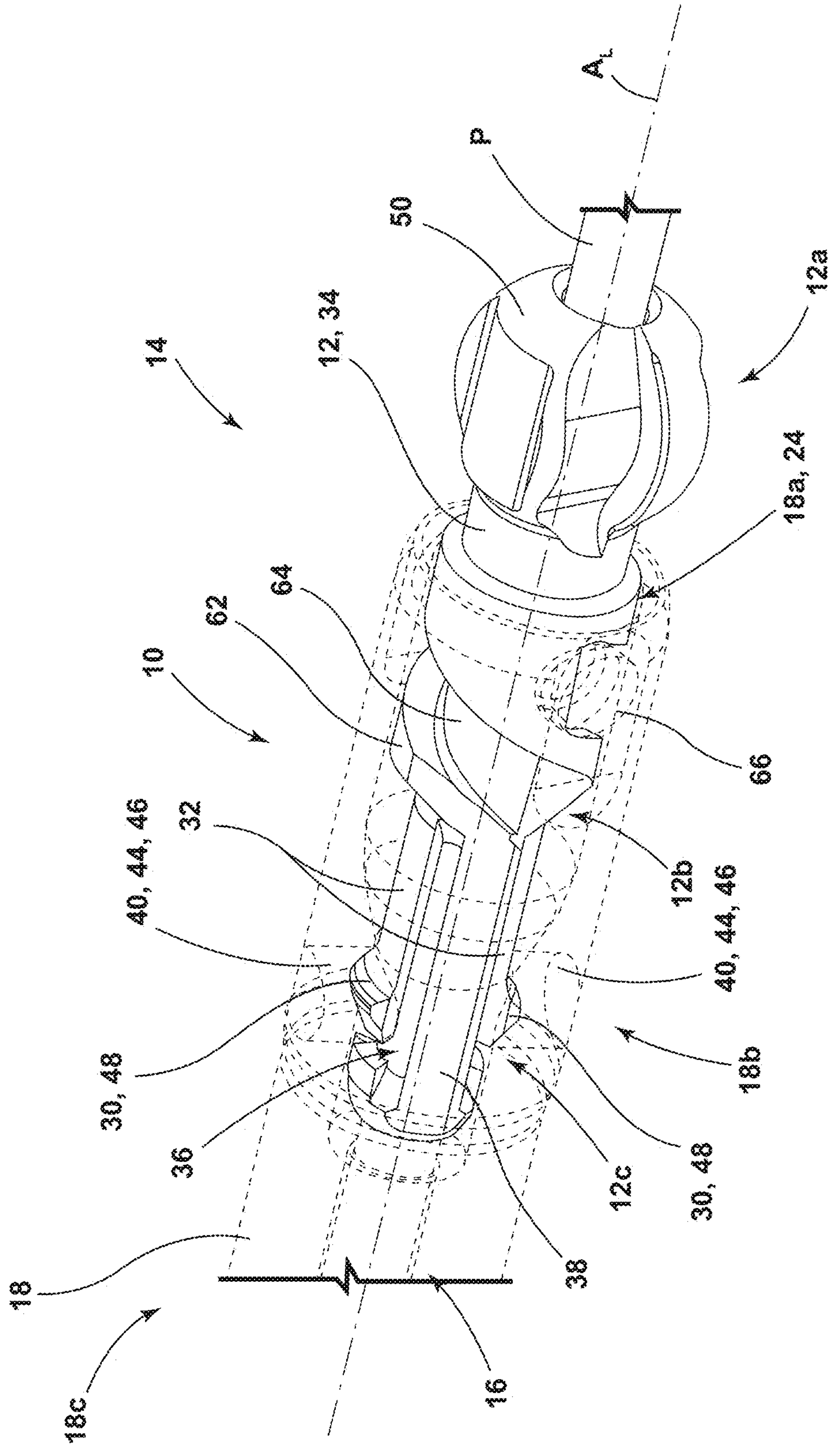
FIG. 2 is a partially transparent, projected assembly view of a coupling interface of a surgical accessory engaging a guide pin or wire.

As best demonstrated in FIGS. 1B and 2, the cannula 16 may extend through the surgical accessory 12 from a distal end 12*a* through an intermediate portion 12*b* and into a proximal engagement portion 12*c*. The coupling interface 10 may correspond to the engagement of the intermediate portion 12*b* and the proximal engagement portion 12*c* of the surgical accessory 12 within a receiving opening 24 extending from a distal end portion 18*a* and into an intermediate portion 18*b* of the socket adapter 18. In this configuration, the cannula 16 may extend in alignment with the longitudinal axis $A_L$ through the proximal engagement portion 12*c* of the surgical accessory 12 and into the proximal end portion 18*c* of the socket adapter 18. The continuous passage of the cannula 16 through the surgical accessory 12 and the socket adapter 18 forming the connection assembly 14 may allow the guide pin P to pass through the coupling interface 10 along the longitudinal axis $A_L$.

Figure 1A:
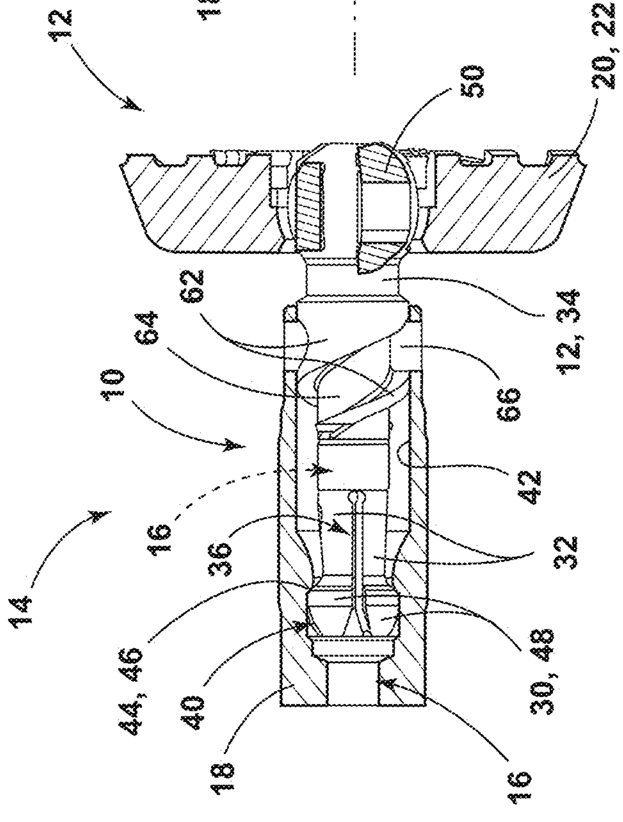
FIG. 1A is a partially hidden, side assembly view of a coupling interface for a surgical accessory.

Various features of the coupling interface 10 are discussed throughout the detailed description in reference to FIGS. 2-5D, however, some exemplary features of the connection assembly 14 may be implemented differently in the examples of FIGS. 1A and 1B relative to the remainder of the examples. In particular, the proximal end portion 12*c* of the surgical accessory 12 may comprise one or more detents 30, protrusions or catches disposed proximate to a terminal end of one or more corresponding flexible arms 32. As shown, the flexible arms 32 are formed by a hollow shaft 34 extending along the longitudinal axis $A_L$ and having the cannula 16 extending therethrough. As best demonstrated in FIG. 1A, the flexible arms 32 may be formed by elongated openings 36 extending from the proximal engagement portion 12*c* that forms the terminal ends of the arms 32 and through a tubular wall 38 proximal to the intermediate portion 12*b*. In this configuration, the flexible arms 32 may deflect into the elongated openings 36 in response to the one or more detents 30 engaging a complimentary retention feature 40 formed in an interior wall 42 along the intermediate portion 18*b* of the socket adapter 18.

Still referring to FIGS. 1A and 1B, the retention feature 40 formed within the interior wall 42 of the socket adapter 18 may correspond to an enlarged cavity or retaining aperture 44 forming a ledge or retention surface 46 that forms a latch or catch to prevent the surgical accessory 12 from withdrawing from the socket 18. The retention surface 46 may be configured to receive a protrusion 48 or retaining clip formed by the detent 30 at the terminal end of the flexible arm 32. In this configuration, the shaft 34 of the surgical accessory 12 may be retained within the receiving opening 24 of the socket adapter 18 by the engagement of the one or more detents 30 of the flexible arms 32 engaging the retention feature 40 of the socket adapter 18. This engagement may prevent inadvertent disengagement while also allowing the accessory 12 to be easily rotated and withdrawn from the receiving opening 24 of the socket adapter 18.

As previously discussed, the distal head 12*a* of the surgical accessory 12 may be in connection with or form one or more surgical tools 20, as exemplified by the reamer 22. In the example shown, the distal head 12*a* of the surgical accessory 12 may correspond to an accessory adapter 50 that may be configured to interchangeably connect with one or more of the surgical tools 20 (e.g., the reamer 22) having various dimensions (e.g., diameters, lengths, etc.) or applications (e.g., coring, reaming, boring, drilling, driving, etc.). Alternatively, the surgical accessory 12 may correspond to a dedicated surgical tool 20. In such cases, the distal head 12*a* of the surgical accessory 12 may correspond to a permanently attached surgical tool 20 affixed to the hollow shaft 34 and extending distally outward along the longitudinal axis $A_L$. The coupling interface 10 provided by the modular connection assembly 14 may be implemented to support the operation of a variety of surgical tools to ensure flexible operation to suit diverse tools and accessories of surgical kits and compatible instruments. Though additional features are demonstrated in FIGS. 1A and 1B, similar structures and elements may be depicted more clearly in FIGS. 2-5D. Accordingly, like elements may be discussed in reference to later examples of the connection assembly 14 for clarity.

Referring now to FIGS. 2-5D, various features of the modular connection assembly 14 are described in further detail. As demonstrated in FIG. 2, a projected view of the connection assembly 14 is shown in engagement with the guide pin P. Similar to the examples depicted in FIGS. 1A and 1B, the coupling interface 10 may comprise a helical or spiraled engagement assembly formed between an exterior surface 58 of the hollow shaft 34 and the interior wall 42 (see, FIG. 4A) formed by a tubular body 60 of the socket adapter 18. As generally demonstrated in FIG. 2 and discussed in further detail in later figures, the coupling interface 10 between the surgical accessory 12 and the socket adapter 18 may comprise a rib 62 or land having a rib thickness $t_w$ that may be formed as a rectangular or angled flange extending outward (e.g., perpendicularly) from the exterior surface 58 and spiraling along the intermediate portion 12*b* at a helix angle ϕ (see FIG. 3B). Between the ribs 62, at least one flute 64 or web may spiral along the longitudinal axis $A_L$ of the hollow shaft 34 between cascading flights of the rib(s) 62, lands, or flanges. Though described in reference to the specific example including the rib 62 or land, it shall be understood that the rib 62 may be implemented as a crest of a thread and the flute 64 or web may correspond to a root formed between flanks of the protruding sidewalls. Accordingly, the at least one flute 62 may be formed between angled sidewalls forming an angular trough or perpendicular sidewalls extending normal to the exterior surface 58 of the tubular body 60. Additionally, the base of the flute 64 may correspond to a flat, rounded, or angled surface depending on the desired engagement with a corresponding engaging profile shape of an engaging protrusion 66 or boss formed within the socket 18. Accordingly, the engagement between the surgical accessory 12 and the socket 18 may be implemented in a variety of ways.

The at least one flute 64 extending between the crest or rib 62 protruding from the hollow shaft 34 may extend from an open end 64*a* formed along the intermediate portion 12*b* to a closed end 64*b* of the flute 64 near the distal head 12*a*. Opposite the flute 64 and extending from the interior wall 42 at the distal end portion 18*a* of the socket 18, the engaging protrusion 66 may extend inward into the receiving opening 24 and toward the longitudinal axis $A_L$. In this configuration, the engagement of the proximal engagement portion 12*c* of the surgical accessory 12 with the receiving opening 24 of the socket adapter 18 may be secured by aligning the engaging protrusion 66 with the open end 64*a* of the flute 64. As the intermediate portion 12*b* of the surgical accessory 12 engages the receiving opening 24 to an increasing penetration depth, the protrusion 66 may traverse the corresponding flute 64, causing the surgical accessory 12 to rotate along the helix angle ϕ until the protrusion 66 reaches the closed end 64*b* of the flute 64. In this configuration, the penetration of the proximal engagement portion 12*c* of the surgical accessory 12 or penetration depth may be limited by the protrusion 66 abutting the closed end 64*b* of the flute 64. The penetration depth may additionally result in the alignment of the one or more detents 30 of the corresponding one or more flexible arms 32 with at least one retaining aperture 44 formed through the tubular body 60 of the socket adapter 18. In this way, the surgical accessory 12 may be secured to the socket adapter 18 via the coupling interface 10.

In the example shown, the closed end 64*b* of the flute 64 may form a positive engagement stop or positive stop of the engagement between the flute 64 of the surgical accessory 12 and the protrusion 66 of the socket 18. In some implementations, the positive stop between the surgical accessory 12 and the socket 18 along the longitudinal axis $A_L$ may be provided by various interacting features (e.g., flanges, variations in diameter, protrusions, etc.) that may create an interference between the surgical accessory 12 and the socket 18 along the longitudinal axis $A_L$. For example, the rotational engagement along the helix angle ϕ of the at least one flute along the longitudinal axis $A_L$ with the receiving socket may cause the surgical accessory to rotationally abut a positive stop between the surgical accessory and the receiving socket. The positive stop may correspond to a shoulder or protrusion extending outward from the exterior surface 58 of the tubular body 60 and/or an interior projection or flange protruding into the socket 18 that may result in a mechanical interference preventing further engagement between the surgical accessory 12 and the socket 18 along a penetration depth extending into the socket 18.

The examples depicted in the figures provide for the protrusions 66 in the form of blunt, cylindrical tabs and the flutes 64 as complementary rectangular channels. However, the protrusions 66 and flutes 64 may generally correspond to mating features having a complementary engaging profile and receiving profile extending along a portion of the longitudinal axis $A_L$ at the helix angle ϕ. For example, in some cases, the engaging profile of the protrusions 66 may correspond to a cone-shaped, chamfered, or triangular profile configured to engage an angled or wedge-shaped receiving profile of the flutes 64. Similarly, the complementary profiles may correspond to a curved or rounded engaging profile of the protrusions 66 with a corresponding receiving profile of the flutes 64. In various implementations, the complementary engaging profile and receiving profile formed by the protrusions 66 and the flutes 64 may be compatible to provide the engagement but have differing profile shapes. For example, the protrusions 66 may correspond to spheroid or rounded protuberances that engage a rectangular or wedge-shaped channel formed by the flutes between the rib 62 or flights. In general, the complementary engaging profiles formed between the protrusions 66 and the flutes 64 may be implemented to provide a secure engagement between the accessory 12 and the socket 18 while preventing binding that may present difficulties in exchanging the surgical accessory 12 with compatible devices as later discussed in reference to FIG. 6.

Figure 3A:
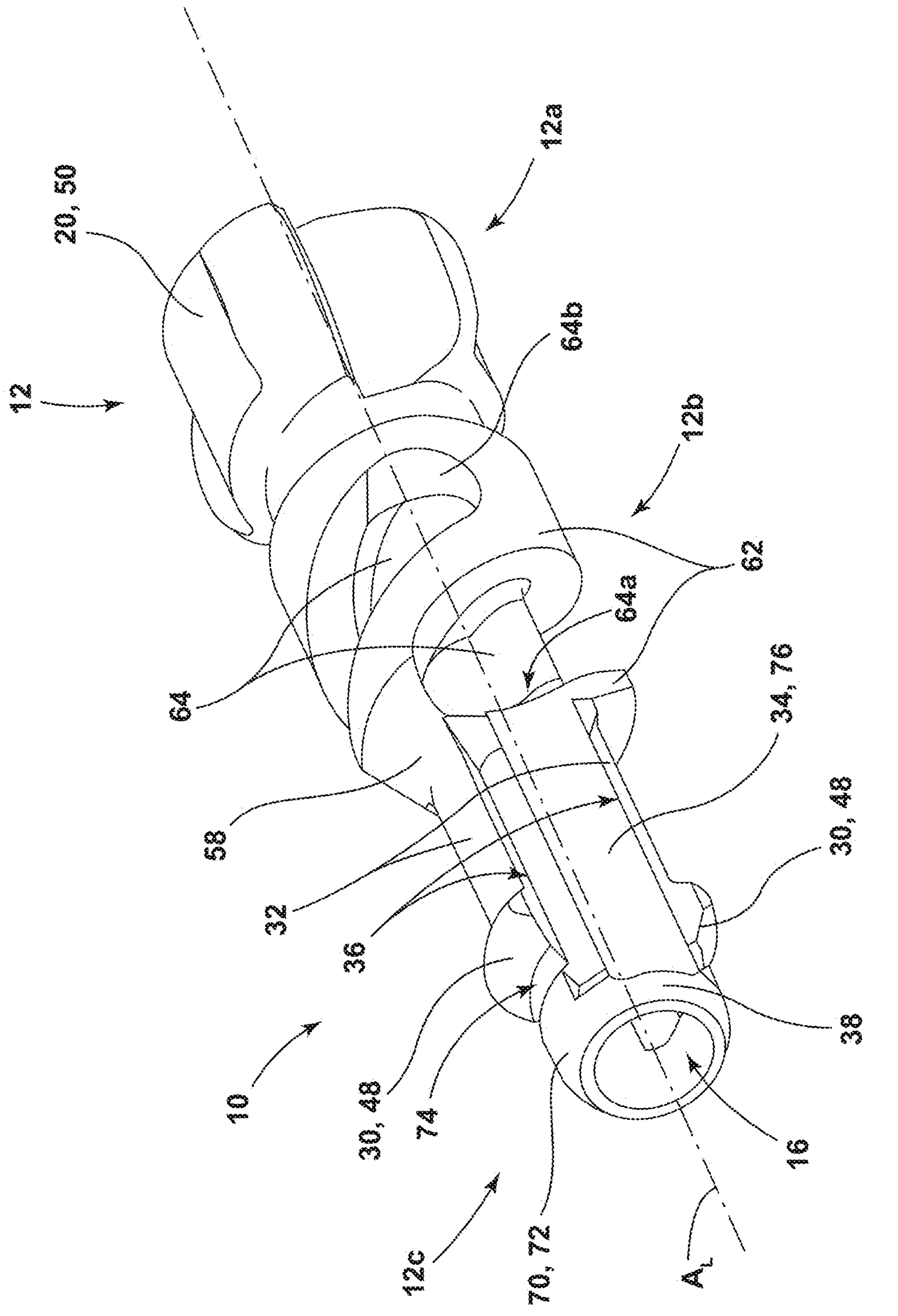
FIG. 3A is a projected view of a male component of a coupling interface for a surgical tool.
Figure 3B:
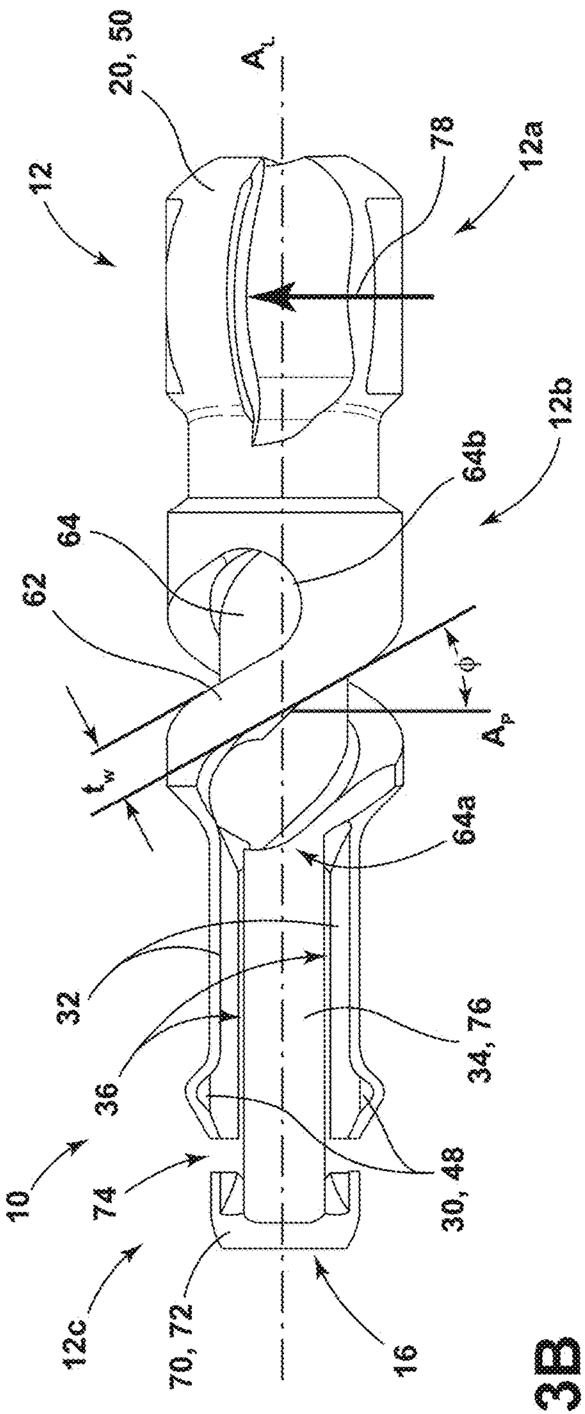
FIG. 3B is a side profile view of a male component of a coupling interface for a surgical tool.
Figure 3C:
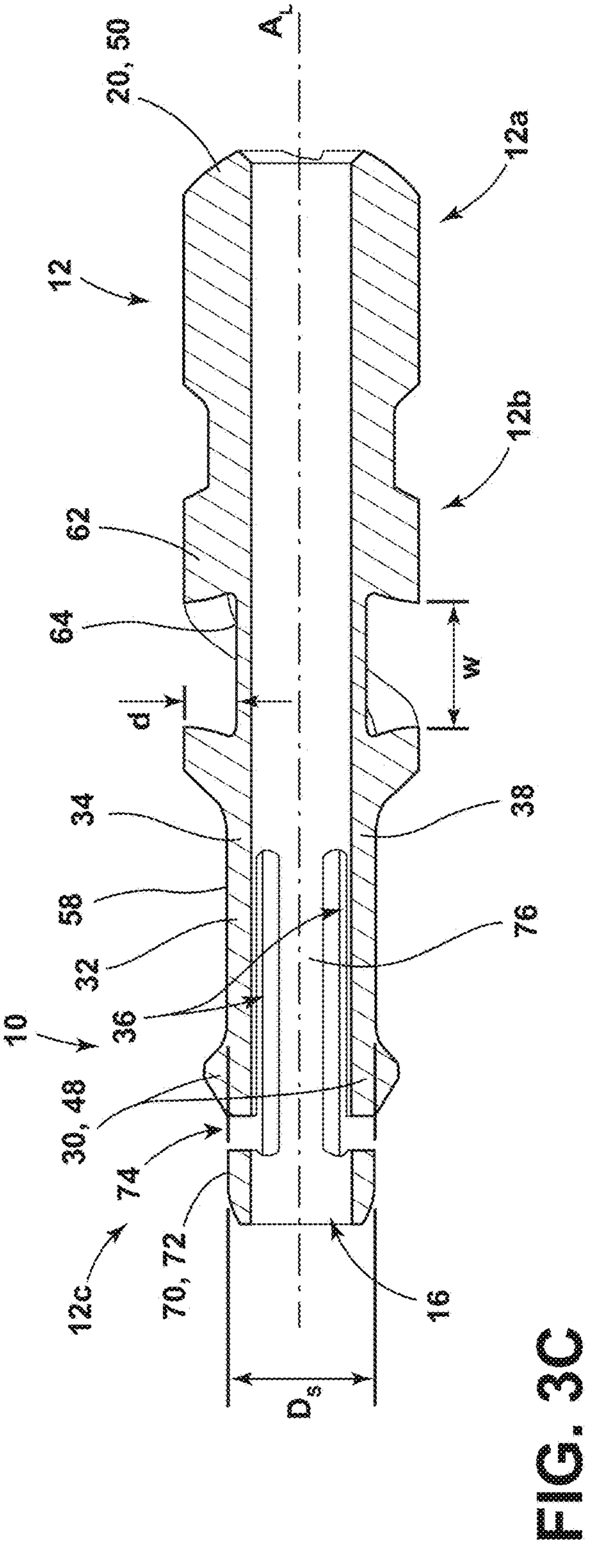
FIG. 3C is a side cross-sectional view of a male component of a coupling interface for a surgical tool.

Referring now to FIGS. 3A-3C, various features of the surgical accessory 12 or male component of the coupling interface 10 are described in further detail. As shown in the foreground of FIG. 3A, the proximal engagement portion 12*c* extends from a tapered proximal end 70 that may flare or expand along the longitudinal axis $A_L$ to a shank diameter $D_S$. The shank diameter $D_S$ may provide for a clearance fit within the receiving opening 24 between the one or more protrusions 66 at the distal end portion 18*a* of the socket adapter 18. In contrast with the example demonstrated in FIGS. 1A and 1B, the detents 30 disposed at the terminal ends of the flexible arms 32 may not form the proximal extent of the exemplary surgical accessory 12 shown in FIGS. 3A-3C. Alternatively, the tapered proximal end 70 may form a tubular lead-in portion 72 leading to the detents 30 at the terminal ends of the flexible arms 32 along the longitudinal axis $A_L$. In this configuration, the engagement of the proximal engagement portion 12*c* of the surgical accessory within the receiving opening 24 and the retaining aperture or apertures 44 may not result in unintentional deflection or bending of the one or more flexible arms 32 outward, away from the longitudinal axis $A_L$ due to interference between the surgical accessory 12 and the socket adapter 18. Instead, the elongated openings 36 demonstrated in the example shown in FIG. 3 may connect with and form distal openings 74 between the distal extent of the flexible arms 32 and the tapered proximal end 70. Additionally, opposing support portions 76 of the tubular wall 38 forming the hollow shaft 34 may be retained to connect and support the tapered proximal end 70 between opposing flexible arms 32. In this configuration, the proximal engagement portion 12*c* of the surgical accessory 12 may maintain a robust structure while providing form the engagement of the detents 30 or protruding ramps 48 disposed at the terminal ends of the flexible arms 32 with the retaining apertures 44 of the socket adapter 18.

As best demonstrated in FIG. 3B, the opposing support portions 76 extending along the proximal engagement portion 12*c*, extending along the shank diameter $D_S$, may provide for a path for the one or more engaging protrusions

66 to slide along the proximal engagement portion 12*c* and engage the open end 64*a* of the flute 64. As previously discussed, the flute 64 may be formed by one or more ribs 62. As shown, the coupling interface 10 may be formed by a plurality of ribs 62 (e.g., two adjacent or successive ribs or lands) aligned with the opposing support portions 76 of the hollow shaft 34. In this configuration, opposing bosses or protrusions 66 of the socket adapter 18 may engage the open ends 64*a* of two corresponding flutes 64. The rotational engagement of the bosses or protrusions 66 within the opposing flutes 64 may provide for the rotational engagement of the surgical accessory 12 within the receiving opening 24 traversing along the longitudinal axis $A_L$ until the protrusions 66 engage the closed ends 64*b* of the flute 64. As with the previously discussed example of FIGS. 1A and 1B, the penetration depth of the proximal engagement portion 12*c* in coordination with the engagement of the protrusions 66 with the closed ends 64*b* of the flutes 64 may align the protruding ramps 48 forming the detents 30 of the flexible arms 32 with corresponding retaining apertures 44 of the socket adapter 18.

The spiraled or auger-like configuration of the coupling interface 10 may be rotationally aligned or handed with the rotational direction of the corresponding surgical tools 20. For example, as shown, the helix angle ϕ is configured having a righthanded configuration of the flute 64 that runs clockwise along the length of the hollow shaft 34. In operation, a corresponding clockwise rotation of the surgical accessory 12 and the surgical tool 20 may result in torsion from an applied torque 78. The applied torque may result as a responsive force caused by friction or cutting pressure applied from the surgical tool 20 back into the hollow shaft 34 of the surgical accessory 12. In operation, the applied torque 78 may result in the closed end 64*b* of the flute 64 being pressed against the engaging protrusion 66 of the socket adapter 18, effectively tightening or maintaining the engagement of the coupling interface 10. In this configuration, the operation of the surgical tool 20 may ensure that the mechanical connection between the surgical accessory 12 and the socket adapter 18 is fully engaged and stable throughout the operation of the associated tool 20.

As previously discussed, the helical design of the at least one flute 64 may ensure that the operation of the surgical tool 20 locks or maintains the connection provided by the coupling interface 10. Additionally, some aspects or characteristics of the rib 62, flute 64, and/or engaging protrusion 66 may be configured to ensure that the coupling interface 10 is easily engaged by a user while also preventing the surgical accessory 12 from binding within the socket adapter 18. As demonstrated in FIG. 3B, the helix angle ϕ is approximately 30° as measured relative to a transverse or perpendicular axis $A_P$ that extends perpendicularly through the longitudinal axis $A_L$. In various implementations, the helix angle ϕ may range from approximately 15° to 70°, 20° to 50°, or in some cases 25° to 40°. The at least one flute 64 formed by the flighting or ribs 62 may correspond to a wide opening having a width W greater than or equal to a depth D. In this configuration, the corresponding cross-sectional surface area of the closed end 64*b* of the flute 64 that engages the engaging protrusion 66 may be sufficiently large to transfer the applied torque 78 from the surgical accessory 12 into the socket adapter 18 without resulting in significant wear or deformation of the closed end 64*b* or the protrusion 66. Additionally, the wide opening formed by the at least one flute 64 may be configured to receive a corresponding wide or blunt boss or protrusion extending from the interior wall 42 of the socket adapter 18, which may limit the potential for binding between the protrusion 66 and the corresponding walls of the ribs 62 forming the flute 64.

As previously discussed, the distal head 12*a* of the surgical accessory 12 is shown in the form of an accessory adapter 50 that may be configured to mechanically couple with various surgical tools 20. However, in various implementations, the distal head 12*a* may correspond to a dedicated surgical tool 20. In such implementations, the accessory adapter 50 may be replaced by one or more dedicated surgical tools 20 affixed to or formed at the distal end portion of the hollow shaft 34. Though the tools described in reference to the surgical accessory 12 are sometimes discussed in reference to as surgical tools 20, it shall be understood that other surgical tools or compatible surgical accessories 12 may be connected to the socket adapter 18 and implemented based on the teachings of the disclosure. Accordingly, the examples provided in this detailed description shall not be considered limiting to the scope of the appended claims unless expressly stated otherwise.

Figure 4A:
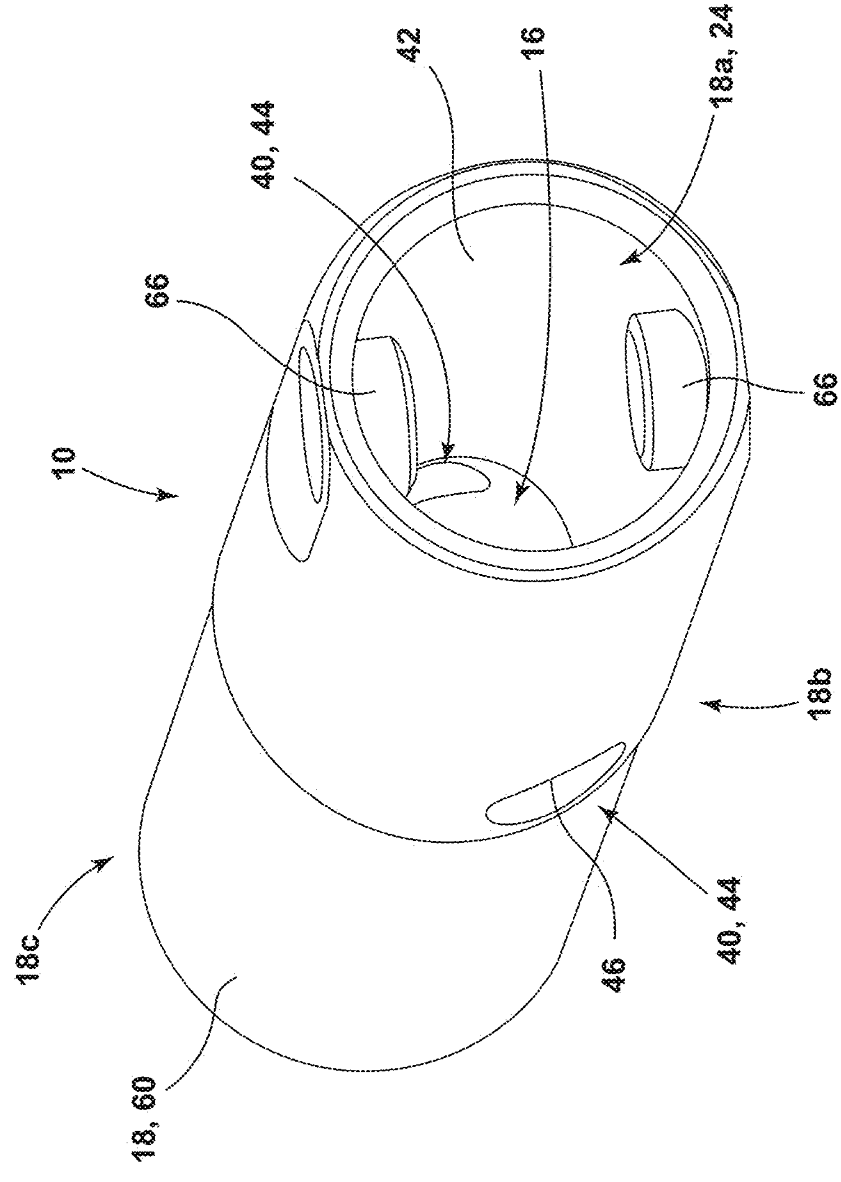
FIG. 4A is a projected view of a female component of a coupling interface for a surgical tool.
Figure 4B:
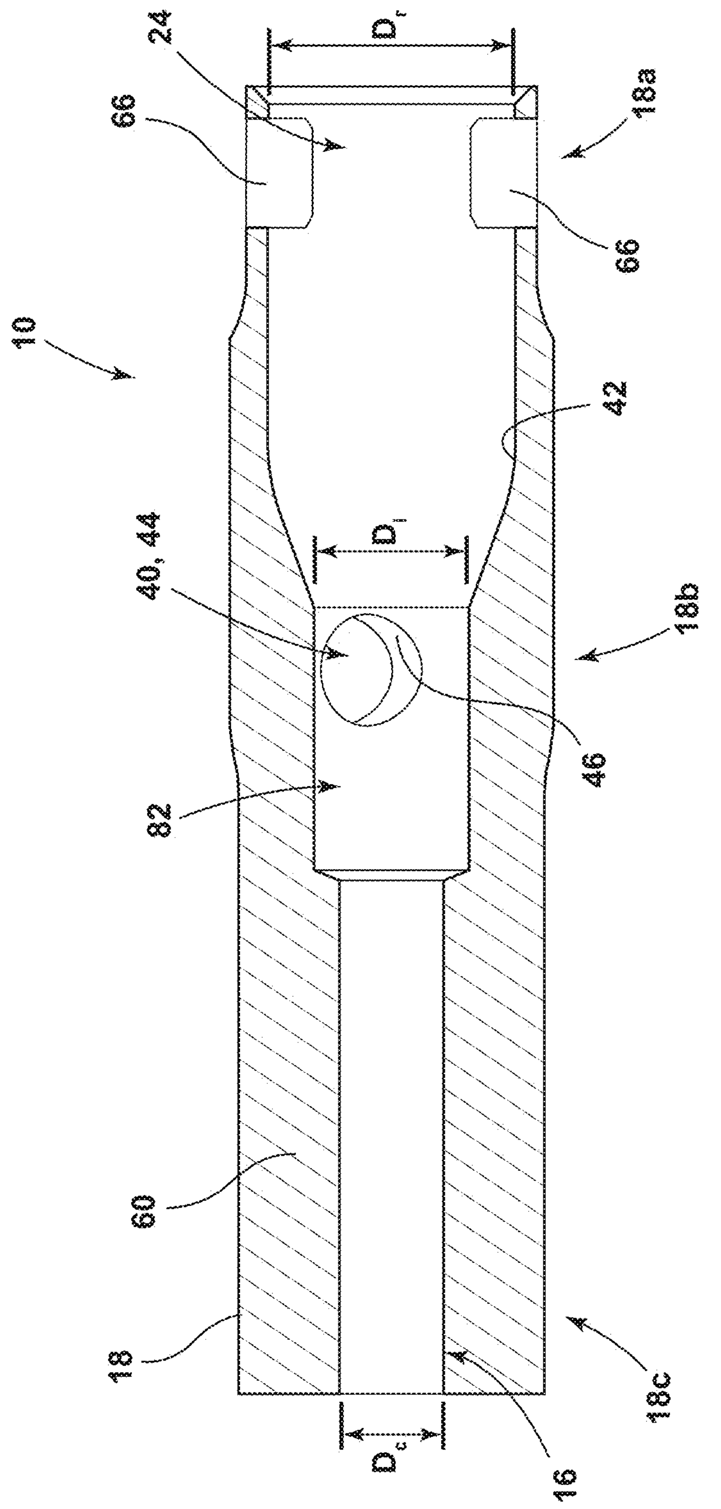
FIG. 4B is a side cross-sectional view of a female component of a coupling interface for a surgical tool.
Figure 5A:
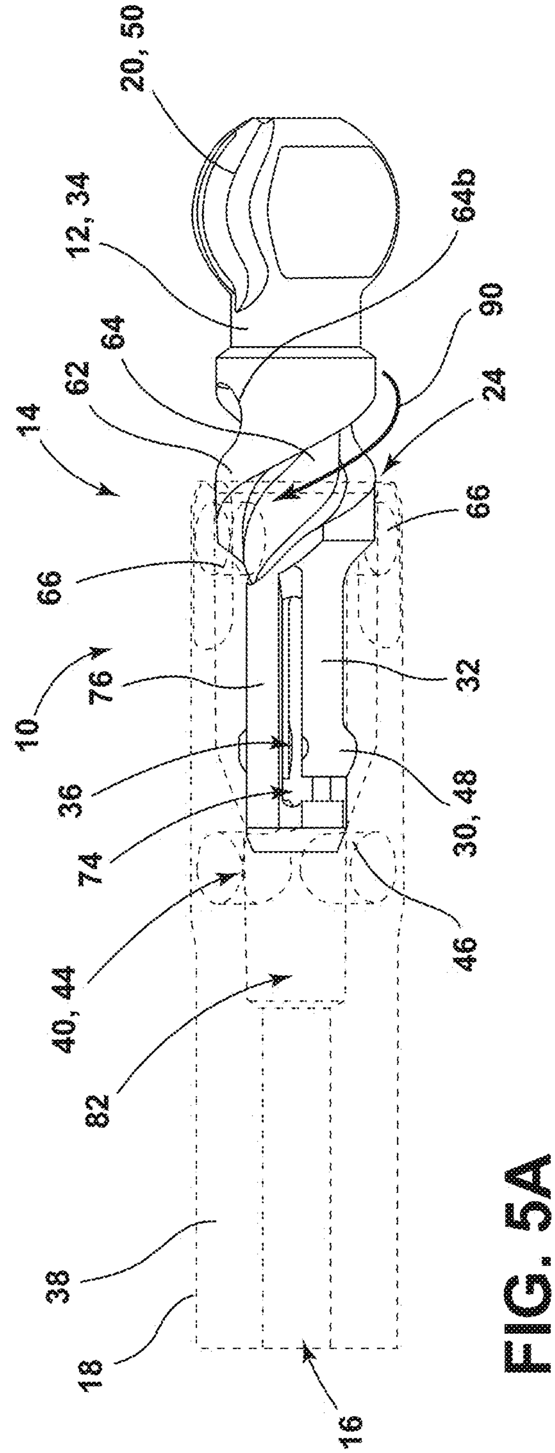
FIG. 5A is a side projected view of an assembly operation connecting a surgical tool to a coupling interface.
Figure 5B:
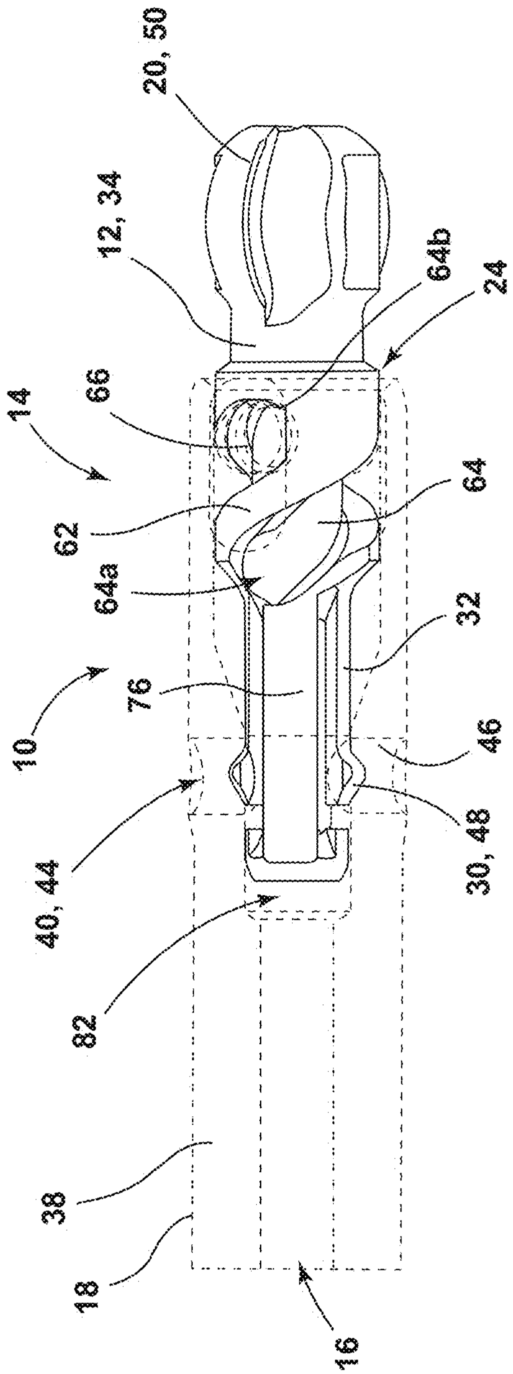
FIG. 5B is a side projected view of an assembly operation connecting a surgical tool to a coupling interface.
Figure 5C:
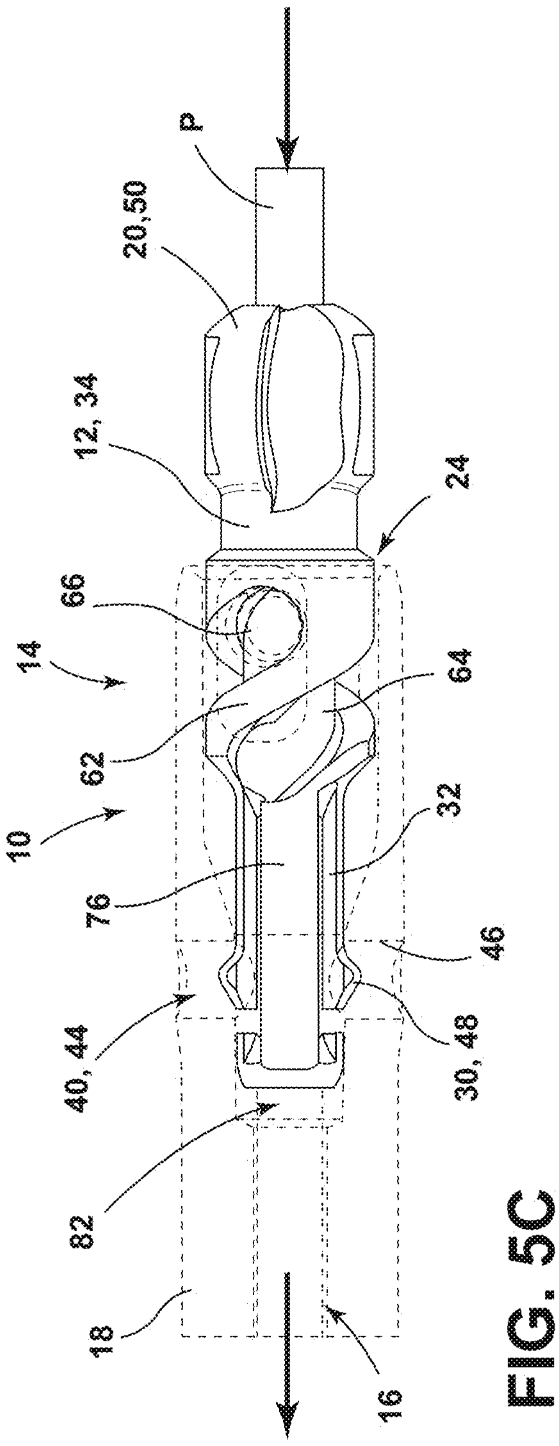
FIG. 5C is a side projected view of a coupling interface for a surgical accessory engaging a guide pin or wire in accordance with the wire.
Figure 5D:
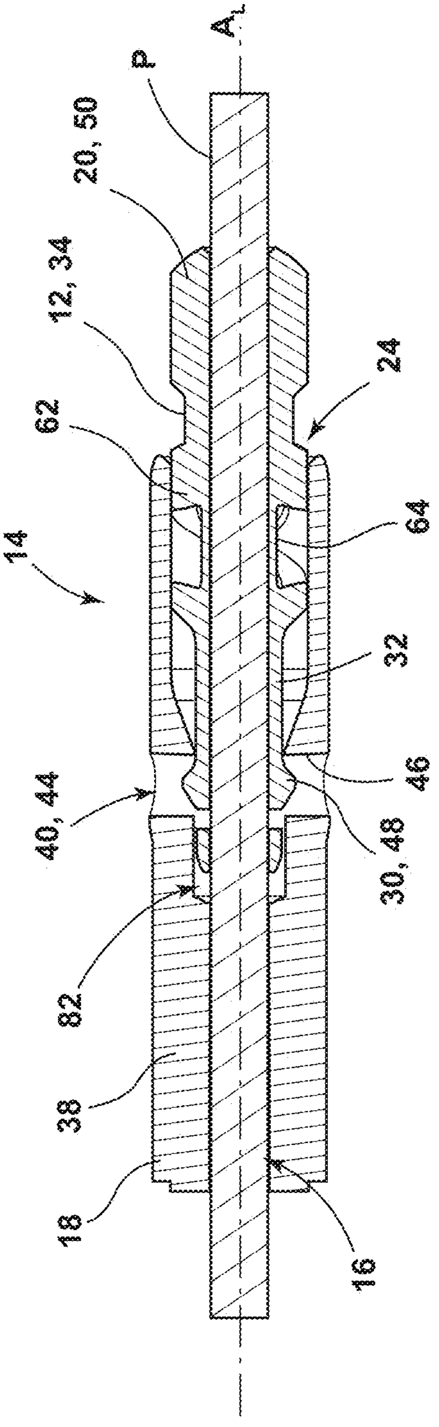
FIG. 5D is a cross-sectional view of the modular connection assembly extending along a longitudinal plane aligned with a retention feature demonstrating the engagement of the coupling interface with a guide pin.

Referring now to FIGS. 4A and 4B, detailed views of the socket adapter 18 are shown and described in further detail. As best demonstrated in FIG. 4B, the interior wall 42 formed by the tubular body 60 of the socket 18 may extend from the receiving opening 24 at the distal end portion 18*a* to an intermediate opening 82 extending along the intermediate portion 18*b*. The intermediate opening 82 may extend along the intermediate portion 18*b* of the socket adapter 18 to the cannula 16 which may extend along the proximal end portion 18*c*. The receiving opening 24, intermediate opening 82, and the cannula 16 may each have sequentially decreasing cross-sectional areas defined by the interior wall 42 of the tubular body 60 converging toward the longitudinal axis $A_L$ along the length of the socket adapter 18 from the distal end portion 18*a* to the proximal end portion 18*c*. In this configuration, the receiving opening 24 may have a first diameter or receiving diameter $D_r$, the intermediate opening 82 may have a second diameter or intermediate diameter $D_i$, and the cannula 16 may have a third diameter or cannula diameter $D_c$. As shown, the receiving diameter $D_r$ may be greater than the intermediate diameter $D_i$ and the intermediate diameter $D_i$ may be greater than the cannula diameter $D_c$. The configuration of the tubular body 60 may provide for the engagement with various cannulated surgical accessories 12 while also providing for the various features of the coupling interface 10 as described herein.

As previously discussed, the detents 30 of the flexible arms 32 of the surgical accessory 12 may engage one or more retention apertures 44. In the example shown, a plurality of retention apertures 44 are formed through the intermediate portion 18*b* of the tubular body 60 as a continuous cylindrical through-hole. In this configuration, the retaining apertures 44 form corresponding openings on opposing sides of the tubular body 60 configured to receive the protruding ramps 48 of the opposing flexible arms 32 described in reference to FIGS. 3A-3C. As shown in FIGS. 1, 3, and 4; the detents 30 may engage the retention feature 40 formed by the socket adapter 18 to ensure that the spiraling or helical engagement between the surgical accessory 12 and the socket adapter 18 is maintained when the connection assembly 14 and surgical tool 20 are idle or do not have the applied torque 78 otherwise securing the connection of the coupling interface 10. Each of the features of the surgical accessory 12 and the socket adapter 18 may provide for a variety of benefits related to the assembly and operation of the modular connection assembly 14 in the corresponding coupling interface 10 as further described in reference to FIG. 5A-5D.

Referring now to FIGS. 5A-5D, the assembly and operation of the modular connection assembly 14 is described in further detail. As demonstrated in FIG. 5A, the engagement of the surgical accessory 12 with the socket adapter 18 may be initiated by inserting the proximal engagement portion 12*c* into the receiving opening 24. As the proximal engagement portion 12*c* extends into the cavity from the receiving opening 24 along the longitudinal axis $A_L$, the opposing support portions 76 may slide against the engaging protrusions 66 protruding into the receiving opening 24 from the interior wall 42. Once the protrusions 66 reach the corresponding flutes 64 positioned on opposing sides of the hollow shaft 34, the engaging protrusions 66 may engage the open ends 64*a* of the corresponding flutes 64. Following the engagement of the protrusions 66 within the flutes 64, the translation of the surgical accessory 12 along the longitudinal axis $A_L$ may result in a rotation 90 of the surgical accessory 12 as the protrusions 66 traverse the flutes 64. As demonstrated in FIG. 5B, the rotation 90 and engagement between the surgical accessory 12 and the socket adapter 18 may continue about the longitudinal axis $A_L$ until the outer surface of the protrusions 66 engages the closed ends 64*b* of the flutes 64. The rotational engagement between the surgical accessory 12 and the socket adapter 18 may provide for a corresponding rotation about the longitudinal axis $A_L$ that may be defined based on the helix angle $\phi$ and the length of the flutes 64 along the longitudinal axis $A_L$ of the hollow shaft 34. In the example shown, the engagement along the helical path formed by the flutes 64 may result in a quarter turn or 90° rotation of the surgical accessory 12 relative to the socket adapter 18. However, it shall be understood that the rotational engagement and corresponding flute design of the coupling interface 10 may be adjusted to provide for various angular engagement rotations (e.g., 30°, 45°, 90°, 180°, 360°, etc.).

Upon reaching the engagement between the protrusions 66 and the closed end 64*b* of the flutes 64, the protruding ramps 48 or retaining clips associated with the detents 30 of the flexible arms 32 may be aligned with the corresponding retaining apertures 44 formed through the intermediate portion 18*b* of the socket adapter 18. In this configuration, the engagement of the protruding ramps 48 of the flexible arms 32 with the retaining surfaces 46 formed by the retaining apertures 44 of the tubular body 60 may hold the surgical accessory 12 in connection with the socket adapter 18, thereby securing the coupling interface 10. As further demonstrated in FIGS. 5C and 5D, the introduction of the guide pin P through the cannula 16 of the surgical accessory 12 and the socket adapter 18 may lock the protruding ramps 48 in connection with the retention surface 46 formed by the retaining apertures 44 of the tubular body 60. As best demonstrated in FIG. 5D, the guide pin P may occupy the opening of the cannula 16, such that the flexible arms 32 are prevented from deflecting toward the longitudinal axis $A_L$. In this configuration, the engagement of the modular connection assembly 14 with the guide pin P may lock the coupling interface 10, such that inadvertent operations that may loosen the helical engagement of the at least one protrusion 66 with the at least one flute 64 are prevented from disconnecting the modular connection assembly 14. For example, with the guide pin P introduced and extending through the cannula 16, a reverse operation (e.g., counter-clockwise or anti-clockwise) in the specific example shown, would cause the protruding ramps 48 to bind on the retention surfaces 46 of the retaining apertures 44, such that the protrusions 66 may not traverse the flutes 64 and allow the surgical accessory 12 to withdrawal from the socket adapter 18.

Figure 6:
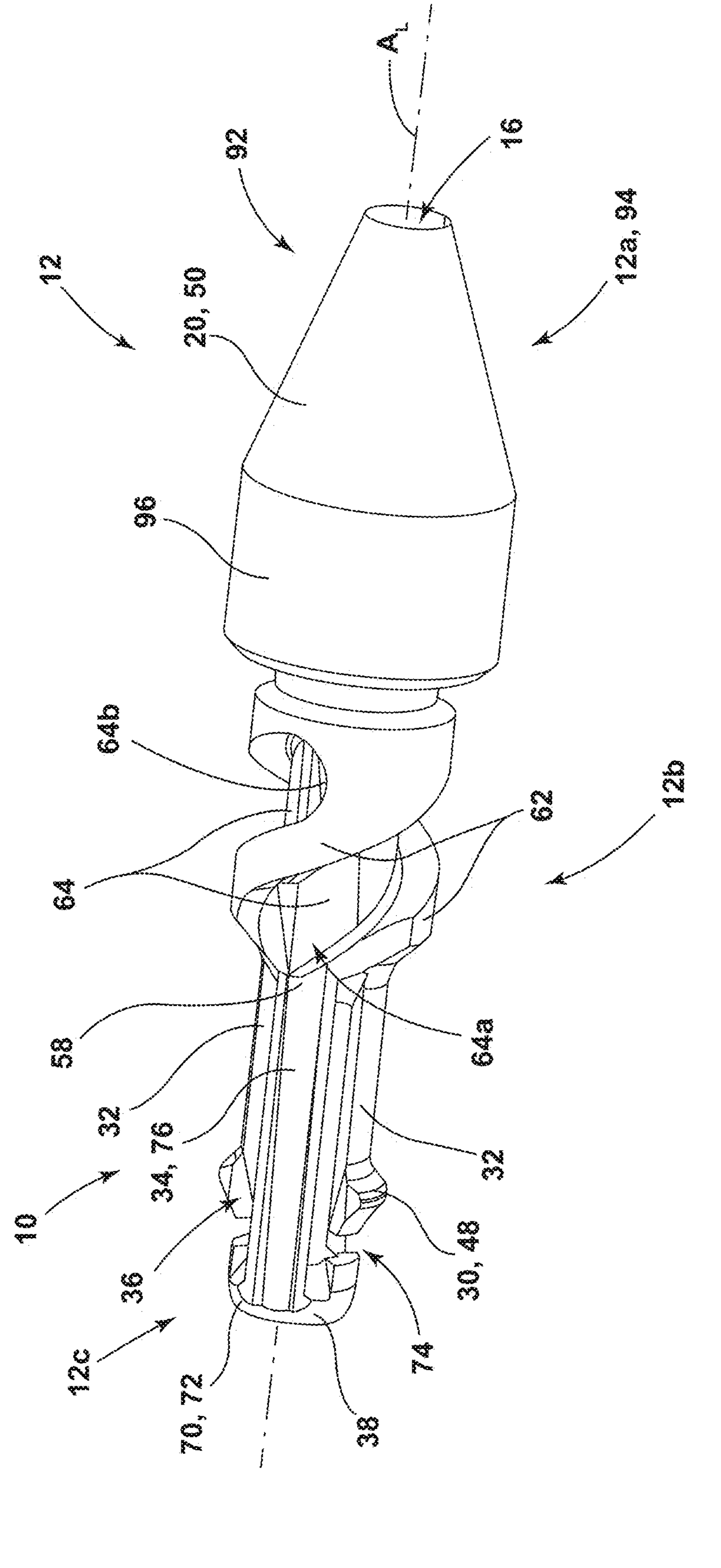
FIG. 6 is a projected view of a male component of a coupling interface for a surgical tool in accordance with the disclosure.

Referring now to FIG. 6, the surgical accessory 12 is shown as a dedicated surgical tool in the form of a cannulated punch 92 or spike. Additional features of the surgical accessory 12 are demonstrated using common reference numerals to identify similar features for clarity. As shown, the punch 92 forms the distal head 12*a* of the surgical accessory 12 as an alternative to the accessory adapter 50 previously described. The punch 92 comprises cone-shaped distal acting end portion 94 expanding toward the proximal engagement portion 12*c* to a cylindrical body 96 having punch diameter corresponding to a lateral extent of the distal head 12*a*. As shown, the cannula 16 extends centrally through the distal head 12*a* along the longitudinal axis $A_L$ and continues through the length of the surgical accessory through the proximal engagement portion 12*c*. Accordingly, the surgical accessory may be implemented having a variety of surgical adapters and/or tools serving as the acting end forming the distal head 12*a*. In various implementations, the coupling interface 10 provided by the modular connection assembly 14 may be implemented to support the operation of a variety of surgical tools to ensure flexible operation to suit diverse tools and accessories of surgical kits and compatible instruments. Though the accessory adapter 50 for the reamer 22 and the punch 92 are demonstrated in the examples provided, the surgical accessory 12 may correspond to various surgical tool, adapters, and accessories that may additionally include one of a reamer, a drill, a mill, a punch, a spike, and a boring tool as well as various surgical tools that may be cannulated.

Figure 7A:
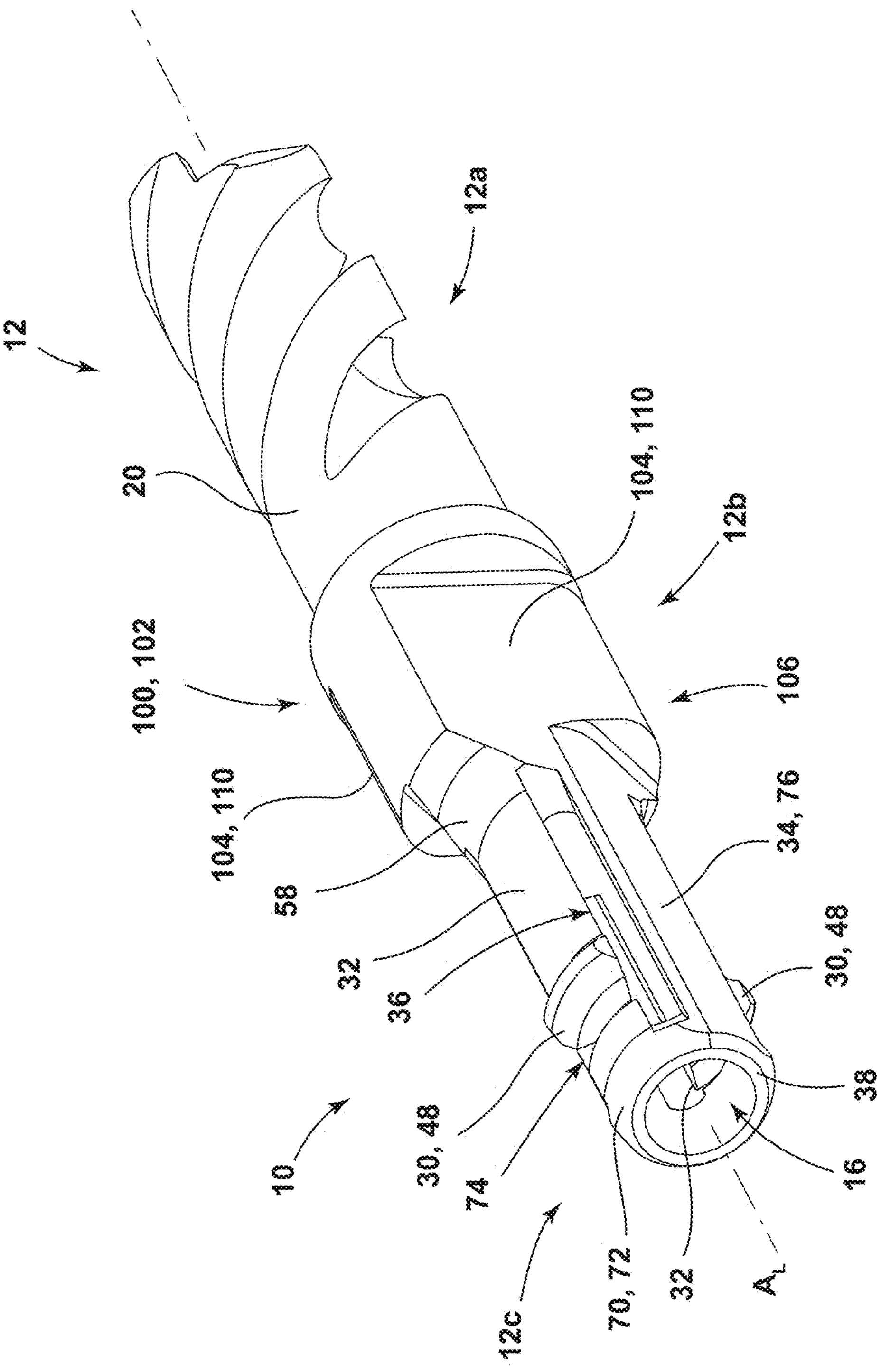
FIG. 7A is a projected view of a male component of a coupling interface for a surgical tool.
Figure 7B:
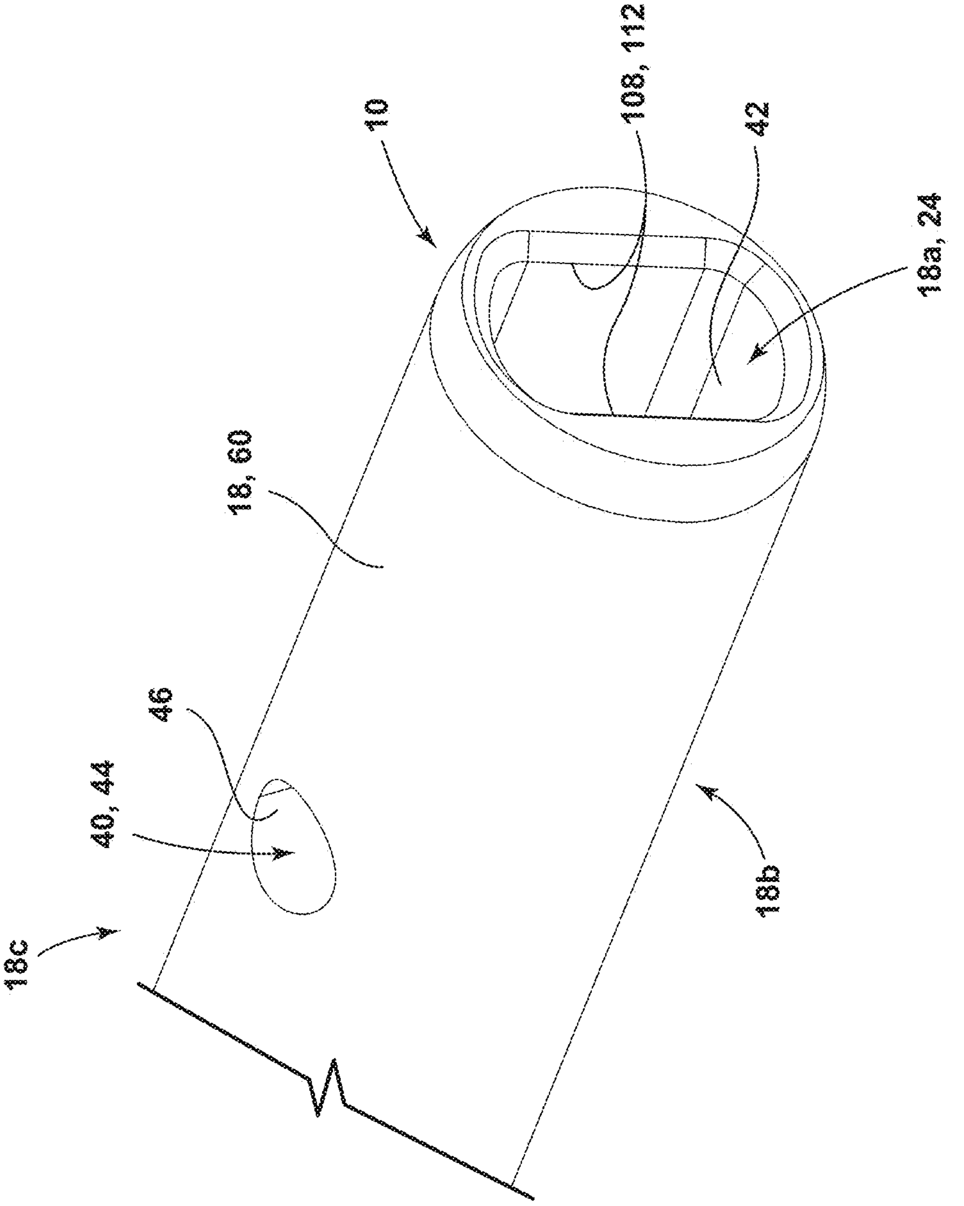
FIG. 7B is a projected view of a female component of a coupling interface for a surgical tool.
Figure 7C:
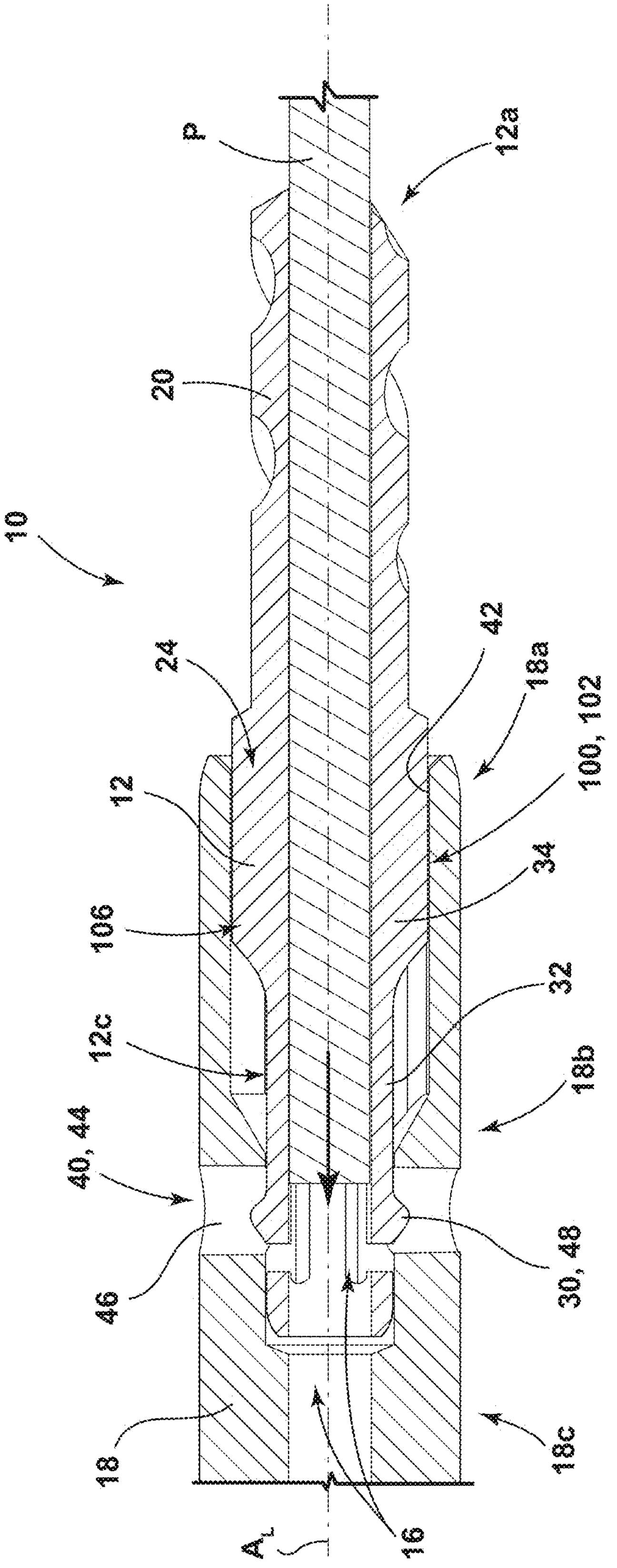
FIG. 7C is a side cross-sectional view of a coupled configuration of a male and female component of a coupling interface in accordance with the disclosure.

Referring now to FIGS. 7A-7C, in some implementations, the coupling interface 10 may comprise a rotary coupling assembly 100 comprising one or more complementary engagement surfaces 102 extending parallel to the longitudinal axis $A_L$. As best shown in FIG. 7A, the surgical accessory 12 may include a cannula 16 extending from the proximal end portion 12*c* to the distal end portion 12*a* along the longitudinal axis $A_L$. Similarly, the proximal end portion 12*c* or engaging end may comprise the one or more detents 30, protrusions or catches disposed proximate to a terminal end of the flexible arms 32. In various implementations, the intermediate portion 12*b* of the surgical accessory 12 may be implemented with various rotational engagement features providing for the coupling interface 10. In the example shown, the complementary engagement surfaces 102 extend along the intermediate portion 12*b* forming at least one engaging feature 104 on a shank 106 of the surgical accessory 12. The at least one engaging feature 104 may be received by a corresponding receiving feature 108 of the socket adapter 18, as best demonstrated in FIG. 7B. In operation, the at least one engaging feature 104 may align with the corresponding receiving feature 108 in the receiving opening 24 rotationally coupling the accessory 12 to the socket adapter 18 about the longitudinal axis $A_L$.

In various examples, the complementary engagement surfaces 102 may correspond to one or more flats or keyed sections formed along the exterior surface 58 of the hollow or cannulated shaft 34. For example, the exterior surface 58 of the shank 106 may form an engaging profile comprising one or more engaging flats 110. In the example shown, a plurality of flats 110 are formed on opposing sides of the cannulated shaft 34 in a double-D or 2-flat profile. Though two of the flats 110 are demonstrated in the example shown, the engaging profile may correspond to various shapes that may rotationally couple the surgical accessory 12 to the socket adapter 18 relative to the longitudinal axis $A_L$. For example, the engaging profile may correspond to a triangle, square, hexagon, star, torx, spline, or various shapes that may include flats or variations from the cylindrical profile of the exterior surface 58 of the cannulated shaft 34. Accordingly, the variations from the cylindrical profile forming the engaging profile may vary in shape, number, or proportion while rotationally coupling the complementary engagement surfaces 102 of the surgical accessory 12 to the socket adapter 18.

In correspondence with the one or more engaging features 104 or engaging flats 110 forming the engaging profile, complementary receiving features 108 or receiving flats 112 may be formed by the receiving aperture 24 of the tubular body 60 of the socket adapter 18. As depicted in FIG. 7C, surgical accessory 12 is shown mated to the socket adapter 18 with the complementary engagement surfaces 102 aligned withing the receiving opening 24. As previously discussed, the detents 30 may engage the corresponding retention features 40 or apertures 44 of the socket adapter 18. In this configuration, the shank 106 of the surgical accessory 12 may be retained within the receiving opening 24 of the socket adapter 18 by the detents 30. The engagement of the detents 30 with the retention features 40 or apertures 44 may ensure the surgical accessory 12 is secured to the socket adapter 18 while also allowing the shank 106 of the surgical accessory to be readily withdrawn from the socket adapter 18 to exchange surgical accessories to accomplish various steps or procedures.

As previously discussed, the introduction of the guide pin P through the cannula 16 of the surgical accessory 12 and the socket adapter 18 may lock the protruding ramps 48 in connection with the retention surface 46 formed by the retaining apertures 44 of the tubular body 60. As best demonstrated in FIG. 7C, the guide pin P may occupy the opening of the cannula 16, such that the flexible arms 32 are prevented from deflecting toward the longitudinal axis $A_L$. In this configuration, the engagement of the modular connection assembly 14 with the guide pin P may lock the coupling interface 10, such that the engagement between the shank 106 and the receiving opening 24 of the socket adapter 18 is restrained from separating or disengaging along separating along the longitudinal axis $A_L$. For example, with the guide pin P introduced and extending through the cannula 16, the detents 30 may be forced into fixed positions within the apertures 44, such that the surgical accessory 12 is bound to the socket adapter 18. Further, upon withdrawal of the pin P or wire from the coupling interface 10, the surgical accessory 12 may be removed or separated from the socket adapter 18 by applying limited force to withdraw the shank 106 from the socket adapter 18.

In various implementations, the connection assembly 14 described herein may provide for improved operation by ensuring a secure connection between the surgical accessory 12 and the socket adapter 18. The secure connection is further maintained while limiting the possibility of unintended binding that may cause delays in surgical operations due to hardships resulting from removing the surgical accessory 12 from the socket adapter 18. Accordingly, in various implementations, the disclosure may provide for an improved coupling interface 10 that may secure the modular connection assembly 14 for operations associated with pin-guided or wire-guided procedures. Though specific examples are described throughout the detailed description, it shall be understood that modifications and combinations of the disclosed examples, as well as equivalent structures, may be understood by those skilled in the art. Accordingly, the examples provided by the disclosure should be considered nonlimiting unless expressly stated otherwise.

According to some aspects of the disclosure, a rotary surgical accessory for a surgical tool comprises a shaft extending along a longitudinal axis from a distal head to a proximal engagement interface. At least one rib protrudes from the shaft along an intermediate portion between the distal head and the proximal engagement portion. The at least one rib forming at least one flute at a helix angle along the intermediate portion and a detent in connection with the proximal engagement interface, wherein the detent engages a complementary retention feature of a receiving socket.

According to various aspects, the disclosure may implement one or more of the following features or configurations in various combinations:

- a cannula extends through the shaft forming a tubular body extending along the longitudinal axis from the distal head to the engagement interface;
- the cannula is configured to receive a guide pin or wire extending along the longitudinal axis through the shaft, wherein the guide pin extending through the cannula binds the detent to the complementary retention feature;
- at least one flute is configured to receive at least one engaging protrusion extending from an interior wall of the receiving socket;
- at least one flute comprises a plurality of flutes angularly distributed about the longitudinal axis;
- the plurality of flutes comprises a first flute and a second flute positioned on opposing sides of the shaft and extending in parallel along the helix angle;
- at least one flute comprises a terminal end forming a positive stop protruding into a channel formed by the flute;
- the helix angle of the at least one flute has a handedness aligned with a rotational cutting direction of the rotary surgical accessory;
- a rotational engagement along the helix angle of the at least one flute along the longitudinal axis with the receiving socket causes the surgical accessory to rotationally abut a positive stop between the surgical accessory and the receiving socket;
- the helix angle is defined relative to a transverse axis perpendicular to the longitudinal axis and is between 20° and 60°;
- the detent comprises a protrusion extending outward from the longitudinal axis that engages a retaining aperture of the receiving socket;
- the proximal engagement interface comprises at least one flexible arm in connection with the shaft and the protrusion is disposed proximate a terminal end of the flexible arm;
- at least one flexible arm is formed by the shaft along the proximal engagement interface as an elongated portion of the tubular body defined by an opening formed through a shaft wall of the tubular body;
- the distal head comprises one of a reamer, a drill, a mill, a punch, a spike, and a boring tool; and/or
- the distal head comprises an adapter configured to detachably engage an interchangeable cutting tool, wherein the cannula extends through the interchangeable cutting tool along the longitudinal axis.

According to another aspect of the disclosure, a coupling interface for a surgical tool comprises a socket adapter including an adapter body having a receiving opening formed by an interior wall with at least one protrusion extending into the receiving opening from the interior wall.

A rotary accessory comprises a shaft extending along a longitudinal axis from a distal head to a proximal engagement interface with at least one rib protruding from the shaft and spiraling along an intermediate portion between the distal head and the proximal engagement portion, the at least one rib forming at least one flute at a helix angle along the intermediate portion. The shaft is received within the receiving opening and the protrusion rotationally engages the at least one flute along the helix angle engaging the surgical tool to the socket adapter.

According to various aspects, the disclosure may implement one or more of the following features or configurations in various combinations:

- a cannula is formed through the shaft forming the rotary accessory as a tubular body extending along the longitudinal axis from the distal head to the engagement interface;
- the rotary accessory comprises a detent in connection with the proximal engagement interface, wherein the detent engages a complementary retention feature of the socket adapter;
- the complementary retention feature comprises a retaining aperture formed in the interior wall of the adapter body;
- the cannula is configured to receive a guide pin or wire extending longitudinally through the coupling interface, wherein the guide pin extending through the cannula binds the detent to the complementary retention feature;
- the proximal engagement interface comprises at least one flexible arm in connection with the shaft and the detent comprises a protrusion disposed proximate a terminal end of the flexible arm; and/or
- at least one flexible arm is formed by the shaft along the proximal engagement interface as an elongated portion of the tubular body defined by an opening formed through a shaft of the tubular body.

According to yet other aspects of the disclosure, a socket adapter for a rotary accessory comprises an adapter body extending from a proximal end portion to a distal end portion, the distal end portion comprising a receiving opening formed by an interior wall and a cannula extending through the body from the proximal end portion to the distal end portion. At least one protrusion extends into the receiving opening from the interior wall at the distal end portion, and a retaining aperture formed in the interior wall at an intermediate portion between the proximal end portion and the distal end portion, wherein the retaining aperture is configured to receive a detent of an engagement portion of the rotary accessory.

According to various aspects, the disclosure may implement one or more of the following features or configurations in various combinations:

- the receiving opening comprises a first inner diameter configured to receive at least one rib protruding from a shaft along an intermediate portion of the rotary accessory, wherein the at least one protrusion engages at least one flute formed by the rib of the rotary accessory; and/or
- the receiving opening forms a retaining opening having a second inner diameter less than the first diameter, wherein the interior wall of the retaining opening comprises at least one retaining opening configured to receive a detent of the rotary accessory.

According to some aspects of the disclosure, a coupling interface for a surgical tool comprises a socket adapter. The socket adapter comprises an adapter body having a receiving opening formed by an interior wall, the receiving opening forming a receiving surface and at least one receiving aperture formed within the receiving opening. The coupling interface further includes a rotary accessory comprising a shaft extending along a longitudinal axis from a distal head to a proximal engagement interface, wherein an intermediate portion of the shaft forms an engaging surface comprising a profile shape complementary to the receiving surface of the receiving opening, wherein the alignment of the engaging surface with the receiving surface rotationally coupling the rotary accessory to the adapter body about the longitudinal axis; and a detent in connection with the proximal engagement interface, wherein the detent engages the receiving aperture of the socket adapter restricting a translation between the rotary accessory and the socket adapter along the longitudinal axis.

According to various aspects, the disclosure may implement one or more of the following features or configurations in various combinations:

- the engagement surface comprises at least one flat formed along the intermediate portion of the shaft and the receiving surface forms a complementary receiving flat;
- the proximal engagement interface comprises at least one flexible arm in connection with the shaft and the detent comprises a protrusion disposed proximate a terminal end of the flexible arm;
- at least one flexible arm is formed by the shaft along the proximal engagement interface as an elongated portion defined by an opening formed through the shaft; and/or
- a cannula extends through the shaft and is configured to receive a guide pin or wire extending longitudinally through the coupling interface, wherein the guide pin extending through the cannula binds the detent to the receiving aperture.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

The invention claimed is:

1. A surgical accessory for a surgical tool comprising:

a shaft extending along a longitudinal axis from a distal head to a proximal engagement interface;

at least one rib protruding from the shaft along an intermediate portion between the distal head and the proximal engagement interface, the at least one rib forming at least one flute at a helix angle along the intermediate portion; and a detent in connection with the proximal engagement interface, wherein the detent engages a complementary retention feature of a receiving socket.

2. The surgical accessory according to claim 1, wherein a cannula extends through the shaft forming a tubular body extending along the longitudinal axis from the distal head to the proximal engagement interface.

3. The surgical accessory according to claim 2, wherein the cannula is configured to receive a guide pin or wire extending along the longitudinal axis through the shaft, wherein the guide pin extending through the cannula binds the detent to the complementary retention feature.

4. The surgical accessory according to claim 1, wherein the at least one flute is configured to receive at least one engaging protrusion extending from an interior wall of the receiving socket.

5. The surgical accessory according to claim 4, wherein the at least one flute comprises a plurality of flutes angularly distributed about the longitudinal axis.

6. The surgical accessory according to claim 5, wherein the plurality of flutes comprises a first flute and a second flute positioned on opposing sides of the shaft and extending in parallel along the helix angle.

7. The surgical accessory according to claim 4, wherein the at least one flute comprises a terminal end forming a positive stop protruding into a channel formed by the at least one flute.

8. The surgical accessory according to claim 7, wherein the helix angle of the at least one flute has a handedness aligned with a rotational cutting direction of the surgical accessory.

9. The surgical accessory according to claim 1, wherein a rotational engagement along the helix angle of the at least one flute along the longitudinal axis with the receiving socket causes the surgical accessory to rotationally abut a positive stop between the surgical accessory and the receiving socket.

10. The surgical accessory according to claim 1, wherein the helix angle is defined relative to a transverse axis perpendicular to the longitudinal axis and is between 20° and 60°.

11. The surgical accessory according to claim 1, wherein the detent comprises a protrusion extending outward from the longitudinal axis that engages a retaining aperture of the receiving socket, and the proximal engagement interface comprises at least one flexible arm in connection with the shaft and the protrusion is disposed proximate a terminal end of the flexible arm.

12. The surgical accessory according to claim 1, wherein the distal head comprises one of a reamer, a drill, a mill, a punch, a spike, and a boring tool.

13. The surgical accessory according to claim 1, wherein the distal head comprises an adapter configured to detachably engage an interchangeable cutting tool, wherein the cannula extends through the interchangeable cutting tool along the longitudinal axis.

14. A coupling interface for a surgical tool comprising:

a socket adapter comprising:

an adapter body having a receiving opening formed by an interior wall;

at least one protrusion extending into the receiving opening from the interior wall; and a rotary accessory comprising:

a shaft extending along a longitudinal axis from a distal head to a proximal engagement interface;

at least one rib protruding from the shaft and spiraling along an intermediate portion between the distal head and the proximal engagement interface, the at least one rib forming at least one flute at a helix angle along the intermediate portion; and wherein the shaft is received within the receiving opening and the at least one protrusion rotationally engages the at least one flute along the helix angle engaging the surgical tool to the socket adapter.

15. The coupling interface according to claim 14, wherein a cannula is formed through the shaft forming the rotary accessory as a tubular body extending along the longitudinal axis from the distal head to the proximal engagement interface.

16. The coupling interface according to claim 15, wherein the rotary accessory comprises a detent in connection with the proximal engagement interface, wherein the detent engages a complementary retention feature of the socket adapter.

17. The coupling interface according to claim 16, wherein the complementary retention feature comprises a retaining aperture formed in the interior wall of the adapter body, and the cannula is configured to receive a guide pin or wire extending longitudinally through the coupling interface, wherein the guide pin extending through the cannula binds the detent to the complementary retention feature.

18. The coupling interface according to claim 14, wherein the proximal engagement interface comprises at least one flexible arm in connection with the shaft and the detent comprises a protrusion disposed proximate a terminal end of the at least one flexible arm.

19. A surgical coupling assembly for a rotary accessory comprising:

an adapter body extending from a proximal end portion to a distal end portion, the distal end portion comprising a receiving opening formed by an interior wall and a cannula extending through the adapter body from the proximal end portion to the distal end portion, wherein the rotary accessory comprises a shaft extending along a longitudinal axis from a distal head to a proximal engagement interface and at least one rib protruding from the shaft and spiraling along an intermediate shaft portion between the distal head and the proximal engagement interface;

at least one protrusion extending into the receiving opening from the interior wall at the distal end portion, wherein the at least one rib of the rotary accessory forms at least one flute at a helix angle along the intermediate shaft portion that engages the at least one protrusion; and a retaining aperture formed in the interior wall at an intermediate coupling portion of the adapter body between the proximal end portion and the distal end portion, wherein the retaining aperture is configured to receive a detent of the proximal engagement interface of the rotary accessory.

20. The surgical coupling assembly according to claim 19, wherein the receiving opening comprises a first inner diameter configured to receive the at least one rib protruding from the shaft along the intermediate shaft portion of the rotary accessory, wherein the at least one protrusion engages the at least one flute formed by the at least one rib of the rotary accessory.

* * * * *